United States Patent
Massicotte

(10) Patent No.: US 9,693,676 B2
(45) Date of Patent: Jul. 4, 2017

(54) TOROIDAL BALLOON-DRIVEN VEHICLE

(71) Applicant: J. Mathieu Massicotte, North Reading, MA (US)

(72) Inventor: J. Mathieu Massicotte, North Reading, MA (US)

(73) Assignee: J. Mathieu Massicotte, North Reading, MA (US)

( * ) Notice: Subject to any disclaimer, the term of this patent is extended or adjusted under 35 U.S.C. 154(b) by 357 days.

(21) Appl. No.: 14/270,727

(22) Filed: May 6, 2014

(65) Prior Publication Data

US 2014/0336455 A1 Nov. 13, 2014

Related U.S. Application Data

(60) Provisional application No. 61/821,791, filed on May 10, 2013.

(51) Int. Cl.
*A61B 1/04* (2006.01)
*A61B 1/00* (2006.01)

(52) U.S. Cl.
CPC .......... *A61B 1/041* (2013.01); *A61B 1/00082* (2013.01); *A61B 1/00156* (2013.01)

(58) Field of Classification Search
CPC ............ A61B 1/00151; A61B 1/00156; A61B 1/0016
USPC ................. 600/114, 121–125, 154; 73/866.5
See application file for complete search history.

(56) References Cited

U.S. PATENT DOCUMENTS

| | | | |
|---|---|---|---|
| 3,746,003 A | | 7/1973 | Blake et al. |
| 3,797,445 A | * | 3/1974 | Zeimer .................... B63G 8/42 114/312 |
| 4,243,040 A | | 1/1981 | Beecher |
| 4,295,464 A | | 10/1981 | Shihata |
| 4,324,262 A | | 4/1982 | Hall |
| 4,469,100 A | | 9/1984 | Hardwick |
| 4,558,971 A | * | 12/1985 | David ..................... F16L 1/038 156/175 |
| 4,820,270 A | | 4/1989 | Hardcastle et al. |
| 4,927,426 A | | 5/1990 | Dretler |
| 4,946,440 A | | 8/1990 | Hall |
| 5,142,989 A | * | 9/1992 | Suzumori ............ G21C 17/017 104/138.2 |
| 5,300,023 A | | 4/1994 | Lowery et al. |
| 5,374,247 A | | 12/1994 | Lowery et al. |
| 5,562,601 A | * | 10/1996 | Takada ................... A61B 1/005 600/114 |
| 5,571,114 A | * | 11/1996 | Devanaboyina ... A61B 1/00151 606/1 |
| 6,071,234 A | * | 6/2000 | Takada ................. A61B 1/0051 600/101 |

(Continued)

FOREIGN PATENT DOCUMENTS

EP 0200668 11/1986
WO 2005102184 11/2005

*Primary Examiner* — Matthew J Kasztejna
(74) *Attorney, Agent, or Firm* — Gesmer Updegrove LLP

(57) ABSTRACT

A device fashioned in the shape of a toroid is rotated by a mechanism that propels itself in one or more directions based on internal rotation. In one specific example, the toroidal device is a toroidal balloon, where the tread of the toroidal balloon driven vehicle (TBDV) is self-contained and the entire outer surface is dynamic. Such a device is uniquely and ideally suitable for exploration of a tubular structure such as, but not limited to, the alimentary tract.

47 Claims, 15 Drawing Sheets

(56) References Cited

U.S. PATENT DOCUMENTS

| | | | | |
|---|---|---|---|---|
| 6,077,219 A * | 6/2000 | Viebach | A61B 1/00151 | 600/114 |
| 6,218,016 B1 | 4/2001 | Tedeschi et al. | | |
| 6,224,544 B1 * | 5/2001 | Takada | A61B 1/121 | 600/101 |
| 6,240,312 B1 * | 5/2001 | Alfano | A61B 1/00016 | 128/903 |
| 6,461,295 B2 * | 10/2002 | Takada | A61B 1/121 | 600/114 |
| 6,505,525 B2 * | 1/2003 | McGrew | G01M 3/38 | 348/82 |
| 6,508,188 B2 * | 1/2003 | Dong | B63B 1/36 | 114/312 |
| 6,517,477 B1 * | 2/2003 | Wendlandt | A61B 1/00156 | 600/114 |
| 6,648,814 B2 * | 11/2003 | Kim | A61B 1/00156 | 356/241.6 |
| 6,692,484 B1 | 2/2004 | Karpiel et al. | | |
| 6,695,771 B2 * | 2/2004 | Takada | A61B 1/31 | 600/114 |
| 6,824,510 B2 * | 11/2004 | Kim | A61B 1/00156 | 348/84 |
| 6,846,029 B1 * | 1/2005 | Ragner | B25B 9/00 | 294/219 |
| 6,971,990 B2 * | 12/2005 | Ziegler | A61B 1/00156 | 600/101 |
| 7,044,245 B2 * | 5/2006 | Anhalt | B08B 9/045 | 180/9.1 |
| 7,087,011 B2 * | 8/2006 | Cabiri | A61B 1/04 | 600/114 |
| 7,235,046 B2 * | 6/2007 | Anhalt | B08B 9/045 | 180/9.1 |
| 7,387,179 B2 * | 6/2008 | Anhalt | B08B 9/045 | 180/9.1 |
| 7,736,300 B2 * | 6/2010 | Ziegler | A61B 1/00156 | 348/82 |
| 8,343,170 B2 | 1/2013 | Massicotte et al. | | |
| 8,568,298 B2 * | 10/2013 | Allen | A61B 1/00082 | 600/114 |
| 8,672,835 B2 * | 3/2014 | Allen | A61B 1/00082 | 600/114 |
| 8,795,158 B2 * | 8/2014 | Yamakawa | A61B 1/00135 | 600/114 |
| 2001/0008952 A1 * | 7/2001 | Takada | A61B 1/121 | 600/155 |
| 2002/0049365 A1 * | 4/2002 | Takada | A61B 1/0052 | 600/114 |
| 2002/0117097 A1 * | 8/2002 | Dong | B63B 1/36 | 114/67 R |
| 2002/0156347 A1 * | 10/2002 | Kim | A61B 1/00156 | 600/160 |
| 2002/0173700 A1 * | 11/2002 | Kim | A61B 1/00156 | 600/114 |
| 2003/0088152 A1 * | 5/2003 | Takada | A61B 1/00156 | 600/114 |
| 2003/0153866 A1 * | 8/2003 | Long | A61B 1/0008 | 604/28 |
| 2003/0214579 A1 * | 11/2003 | Iddan | A61B 1/00156 | 348/81 |
| 2004/0015182 A1 | 1/2004 | Kieturakis et al. | | |
| 2004/0059290 A1 | 3/2004 | Palasis | | |
| 2004/0199052 A1 * | 10/2004 | Banik | A61B 1/00071 | 600/142 |
| 2005/0154278 A1 * | 7/2005 | Cabiri | A61B 1/04 | 600/407 |
| 2006/0089533 A1 * | 4/2006 | Ziegler | A61B 1/00156 | 600/114 |
| 2006/0173473 A1 * | 8/2006 | Bob | A61B 1/00151 | 606/153 |
| 2006/0261771 A1 * | 11/2006 | Anhalt | B08B 9/045 | 318/568.12 |
| 2006/0264707 A1 * | 11/2006 | Kinney | A61B 1/005 | 600/115 |
| 2006/0270901 A1 * | 11/2006 | Bern | A61B 1/0016 | 600/114 |
| 2007/0173785 A1 | 7/2007 | Ostroot | | |
| 2008/0045790 A1 * | 2/2008 | Ziegler | A61B 1/00156 | 600/114 |
| 2009/0227838 A1 * | 9/2009 | Allen | A61B 1/00151 | 600/114 |
| 2009/0233747 A1 * | 9/2009 | Sheridan | A61B 1/00156 | 475/12 |
| 2010/0198011 A1 * | 8/2010 | Ziegler | A61B 1/00156 | 600/114 |
| 2010/0210900 A1 * | 8/2010 | Allen | A61B 1/00151 | 600/101 |
| 2010/0256448 A1 * | 10/2010 | Smith | A61B 1/00059 | 600/156 |
| 2011/0065988 A1 * | 3/2011 | Eidenschink | A61B 1/00151 | 600/115 |
| 2012/0184816 A1 * | 7/2012 | Ashida | A61B 1/0016 | 600/114 |
| 2012/0271105 A1 * | 10/2012 | Nakamura | A61B 1/00101 | 600/114 |
| 2012/0277530 A1 * | 11/2012 | Yamakawa | A61B 1/00135 | 600/114 |
| 2012/0302831 A1 * | 11/2012 | Ashida | A61B 1/00006 | 600/114 |
| 2013/0158349 A1 * | 6/2013 | Ashida | A61B 1/00133 | 600/109 |
| 2013/0172679 A1 * | 7/2013 | Ashida | A61B 1/00156 | 600/114 |
| 2014/0046133 A1 * | 2/2014 | Nakamura | A61B 1/00156 | 600/114 |

\* cited by examiner

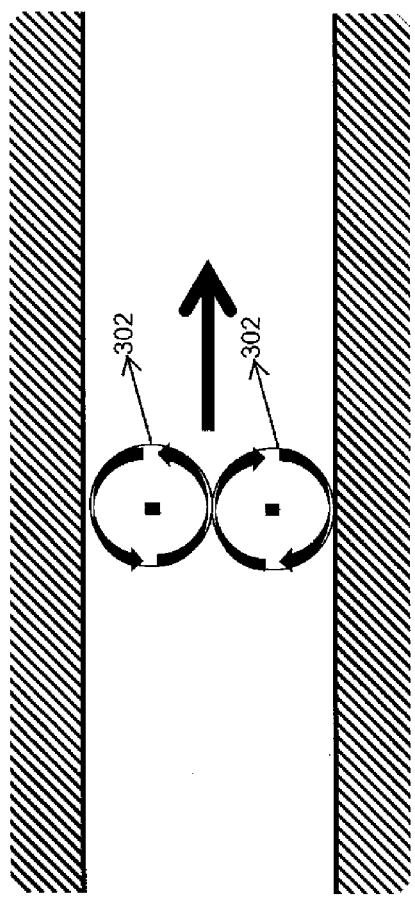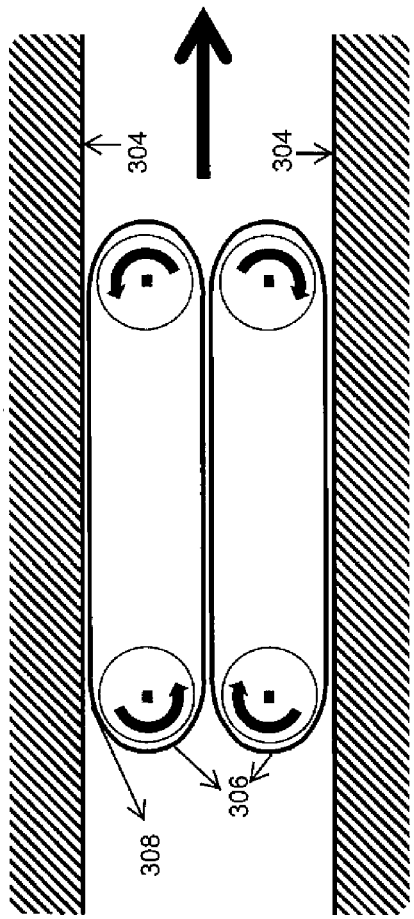
FIG. 3A
FIG. 3B

One version of a drivetrain

Diagram of toroidal balloon

Toroidal balloon-driven Vehicles (TBDV) with associated Utility Components in a SERIAL arrangement Toroidal balloon-driven Vehicles (TBDV) with associated Utility Components in a PARALLEL arrangement

TOROIDAL BALLOON-DRIVEN VEHICLE

PRIORITY INFORMATION

This application claims priority from U.S. Provisional Application 61/821,791 filed May 10, 2013.

BACKGROUND OF THE INVENTION

Field of Invention

The present invention relates generally to medical devices. More specifically, the present invention is related to electrically driven devices for examination of remote areas within, for example, the body, for access of these areas of the body for both diagnostic and therapeutic purposes, and for guiding separate medical devices to remote locations within the body.

Discussion of Prior Art

The bulk of investigative capability of the gastrointestinal tract involves fiberoptic enteroscopy such as upper gastrointestinal (GI) endoscopy and colonoscopy, both of which limit evaluation to the terminal regions of the gastrointestinal tract. Gastroenterologists have limited options for examination of the small bowel. To examine the vast length of jejunum and ileum, x-ray computed tomography, magnetic resonance imaging, capsule endoscopy, other imaging techniques or invasive surgical exploration are required. These current approaches are limited in their diagnostic ability, are expensive and often expose the patient to potential morbidity.

Furthermore, there are few options for treatment of remote pathology since actively controlled access is limited to the terminal segments of the tract. Access to the middle regions of the gut often requires an invasive surgical procedure.

Gastroenterologists and related investigators are actively seeking devices to both examine and treat these regions remote to natural orifices such as the mouth, nose, anus, urethral meatus and ostomy sites.

However, there exists no simple device that allows active and controlled access to remote areas such as, but not limited to, the small bowel in humans and animals, wherein the device can be fashioned for both diagnostic and therapeutic purposes.

Whatever the precise merits, features, and advantages of the above cited references, none achieves or fulfills the purposes of the present invention.

SUMMARY OF THE INVENTION

In one embodiment, the present invention provides an apparatus comprising: (a) a self-contained, transparent toroidal device comprising an inner device surface and an outer device surface, the inner and outer device surfaces comprising inner walls and outer walls configured to form a toroid, where a portion of the outer walls associated with the inner surface are adjacent to each other and are configured to form a channel, and where another portion of the outer walls associated with the outer device surface are configured to contact an external wall; and (b) an internal propelling mechanism located within the inner walls and configured for inverting the inner device surface and outer device surface, with the inversion safely propelling the apparatus without sliding of the outer device surface against any contacted external wall and allowing low friction movement of the apparatus with rotation of the toroidal device, the internal propelling mechanism comprising: a controller, a structural frame with a plurality of rollers disposed thereon, and at least one motor, wherein the controller instructs the motor to rotate the plurality of rollers to cause the inversion of the inner device surface and the outer device surface, with the inversion propelling the apparatus forward or backward without sliding the outer device surface against any contacted external wall.

In another embodiment, the present invention provides an apparatus comprising: (a) a self-contained, transparent, toroidal balloon comprising an inner balloon surface and an outer balloon surface, the inner and outer balloon surfaces comprising inner walls and outer walls configured to form a toroid, where a portion of the outer walls associated with the inner surface are adjacent to each other and are configured to form a channel, and where another portion of the outer walls associated with the outer balloon surface are configured to contact an external wall; and (b) an internal propelling mechanism located within the inner walls and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising: a controller, a structural frame with a plurality of rollers disposed thereon, and at least one motor, wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

In yet another embodiment, the present invention provides an apparatus comprising: (a) a self-contained, transparent, toroidal balloon comprising an inner balloon surface and an outer balloon surface, the inner and outer balloon surfaces comprising inner walls and outer walls configured to form a toroid, where a portion of the outer walls associated with the inner surface are adjacent to each other and are configured to form a channel, and where another portion of the outer walls associated with the outer balloon surface are configured to contact an external wall; (b) an internal propelling mechanism located within the inner walls and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising a structural frame with a plurality of rollers disposed to thereon; and (c) a utility component, where a portion of the utility component is located inside the channel and a remainder portion of the utility component located outside the channel; wherein a controller and a motor are provided in the internal propelling mechanism and/or in the utility component, and wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

The apparatus described in the various embodiments above may also have any of the following disposed either within it and/or on the utility component: batteries, a power supply supplying electrical power, one or more cameras, and/or one or more light sources.

BRIEF DESCRIPTION OF THE DRAWINGS

FIG. 3A depicts a simplified two-dimensional visualization of the rotation of rollers within a confined channel to demonstrate the rotating motion that propels the forward movement of the toroidal balloon driven vehicle (TBDV).

FIG. 3B depicts a two-dimensional coronal view of the present invention's toroidal balloon containing the rotating rollers that make the toroidal balloon driven vehicle (TBDV).

DESCRIPTION OF THE PREFERRED EMBODIMENTS

Figure 1B:
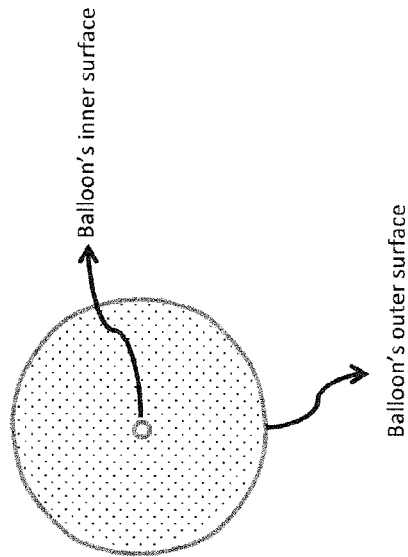
FIG. 1B depicts a transverse section of a toroidal balloon.

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

This device described herein is a vehicle for examination and possible treatment of difficult to reach areas and is based upon the simple geometric shape called a toroid, an elongated donut. The device consists of a balloon fashioned in the shape of a toroid that is rotated by a mechanism that propels itself, the vehicle. Since the tread of the toroidal balloon driven vehicle (TBDV) is self-contained and the entire outer surface is dynamic, the TBDV is uniquely and ideally suitable for exploration of a tubular structure such as, but not limited to, the alimentary tract. It should also be noted that while a toroidal balloon based device is described with regards to many of the figures, the present invention may be implemented in any toroidal-shaped device.

Accordingly, in one embodiment, the present invention provides an apparatus comprising: (a) a self-contained, transparent toroidal device comprising an inner device surface and an outer device surface, the inner and outer device surfaces comprising inner walls and outer walls configured to form a toroid, where a portion of the outer walls associated with the inner surface are adjacent to each other and are configured to form a channel, and where another portion of the outer walls associated with the outer device surface are configured to contact an external wall; and (b) an internal propelling mechanism located within the inner walls and configured for inverting the inner device surface and outer device surface, with the inversion safely propelling the apparatus without sliding of the outer device surface against any contacted external wall and allowing low friction movement of the apparatus with rotation of the toroidal device, the internal propelling mechanism comprising: a controller, a structural frame with a plurality of rollers disposed thereon, and at least one motor, wherein the controller instructs the motor to rotate the plurality of rollers to cause the inversion of the inner device surface and the outer device surface, with the inversion propelling the apparatus forward or backward without sliding the outer device surface against any contacted external wall.

At least a portion of the present invention's toroidal device may be made from nylon or a material allowing low friction rotation of the toroidal device over the internal propelling mechanism.

In another embodiment, the present invention provides an apparatus comprising: (a) a self-contained, transparent, toroidal balloon comprising an inner balloon surface and an outer balloon surface, the inner and outer balloon surfaces comprising inner walls and outer walls configured to form a toroid, where a portion of the outer walls associated with the inner surface are adjacent to each other and are configured to form a channel, and where another portion of the outer walls associated with the outer balloon surface are configured to contact an external wall; and (b) an internal propelling mechanism located within the inner walls and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising: a controller, a structural frame with a plurality of rollers disposed thereon, and at least one motor, wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

While not shown, it should be noted that electronics (e.g., motor, camera, light source, etc.) associated with the various embodiments of the toroidal device of the present invention may be powered by a battery or any suitable source of power. The type of power used should not be used to restrict the scope of the present invention.

Figure 1A:
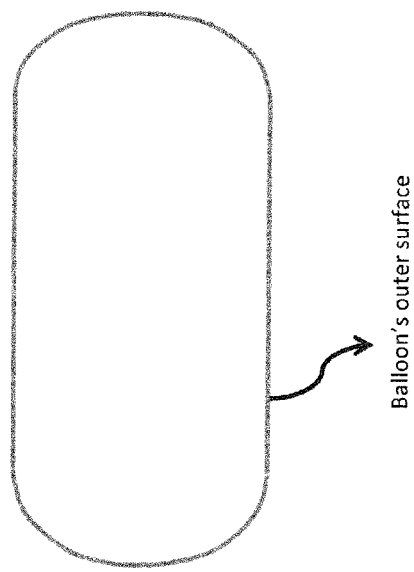
FIG. 1A depicts a toroidal balloon's external appearance.
Figure 1C:
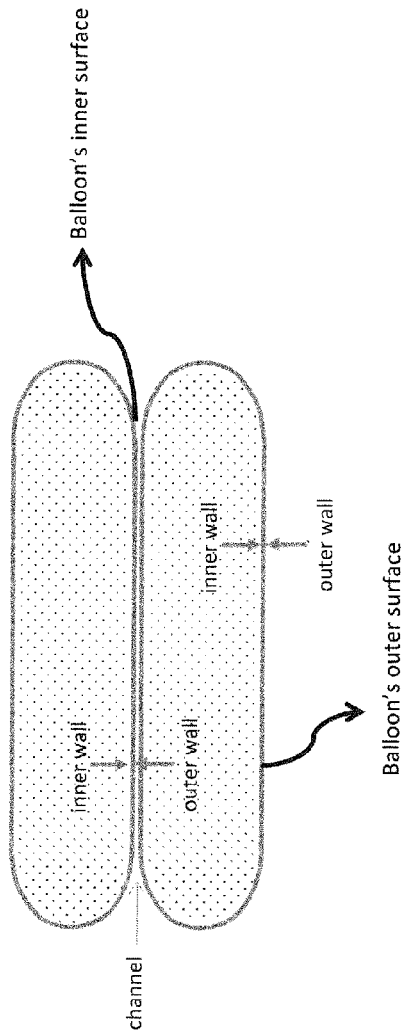
FIG. 1C depicts a coronal section of a toroidal balloon.

A toroidal balloon-driven vehicle (TBDV) is a tool which allows active and controlled access to remote areas such as, but not limited to, the small bowel in humans and animals. The vehicle can be fashioned for both diagnostic and therapeutic purposes. FIGS. 1A-C depict simple diagrams depicting a toroidal balloon in general. FIG. 1A depicts an external view, which is hot dog shaped, although an inner channel is not visible from the outside. FIG. 1B depicts a traverse section (2-D) which shows the balloon's outer surface and the balloon's inner surface. FIG. 1C depicts a coronal section (2-D) showing the balloon's outer surface and the balloon's inner surface.

In one embodiment, the device consists of a toroidal-shaped balloon that propels itself in one or more direction with internal rotation. The present invention's toroidal balloon-driven vehicle may exist solely as a self-contained toroidal balloon or as a compound device constructed with both a toroidal balloon and an associated utility component external to the balloon such as within the toroidal balloon's inner channel. Further, the present invention's toroidal balloon-driven vehicle may be used within body structure such as, but not limited to, the gastrointestinal tract, circulatory system, body cavity, biliary tract, urinary tract, respiratory tract.

In one embodiment, the present invention's toroidal balloon-driven vehicle may contain an internal mechanism for propulsion such as at least one motor, gear system, rotating wheels or rollers, where the mechanism for driving balloon rotation may exist within the balloon. In another embodiment, the present invention's toroidal balloon-driven vehicle may contain an external mechanism for propulsion such as a motor, gear system, rotating wheels, where the mechanism for driving balloon rotation may exist external to the toroidal balloon in a utility component. In yet another embodiment, the present invention's toroidal balloon driven vehicle may contain part-internal and part-external mechanisms for propulsion such as a motor, gear system, rotating wheels or rollers, where the mechanism for driving balloon rotation may exist as combinations of external and internal mechanisms.

In yet another embodiment, the present invention provides an apparatus comprising: (a) a self-contained, transparent, toroidal balloon comprising an inner balloon surface and an outer balloon surface, the inner and outer balloon surfaces comprising inner walls and outer walls configured to form a toroid, where a portion of the outer walls associated with the inner surface are adjacent to each other and are configured to form a channel, and where another portion of the outer walls associated with the outer balloon surface are configured to contact an external wall; (b) an internal propelling mechanism located within the inner walls and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising a structural frame with a plurality of rollers disposed thereon; and (c) a utility component, where a portion of the utility component is located inside the channel and a remainder portion of the utility component located outside the channel; wherein a controller and a motor are provided in the internal propelling mechanism and/or in the utility component (various combinations are envisioned here; i.e., a controller and a motor may be disposed entirely within the utility component, a controller and motor may be disposed within the internal propelling mechanism, a controller may be disposed within the utility component and a motor may be disposed within the internal propelling mechanism, or a controller may be disposed within the internal propelling mechanism and a motor may be disposed within the utility component), and wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

Figure 2:
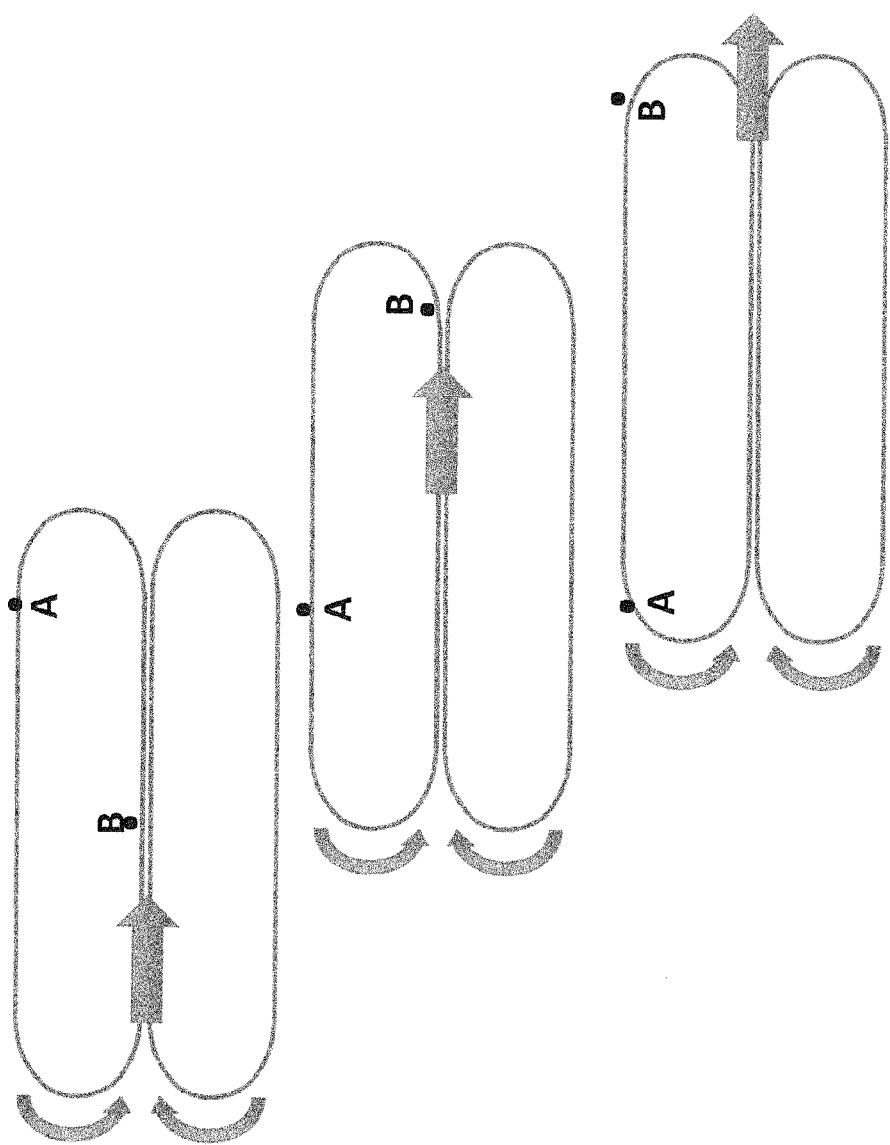
FIG. 2 depicts an example to further understand the inversion aspect of the present invention.

FIG. 2 depicts an example to further understand the inversion aspect of this invention. FIG. 2 shows two points "A" and "B", starting with "A" being on the outer surface and "B" being in the inner surface. As the toroidal balloon's surfaces slide with respect to each other (as shown by the arrows), in the middle figure, point "B" first moves to the right on the toroidal balloon's inside surface, while point "A" simultaneously moves left on the toroidal balloon's outer surface. In the last figure at the bottom, point "B" is inverted as it is now on the outside (in what is now the outside surface of the toroidal balloon) and point "A" has moved more left to the edge on the outside surface of the toroidal balloon.

FIG. 3A depicts a visualization of the rotation in a tubular lumen. Shown is a two-dimensional diagram of rotating wheels 302, where FIG. 3A depicts a simplified version of the idea of rotation using a toroidal or "donut-shaped" balloon in cross section. FIG. 3B depicts the present invention's toroidal balloon 306 that is elongated to move the TBDV with arrows indicating direction of motion of the device based on the rotational motion within. In FIG. 3B, the external surface 308 of the balloon 306 does not slide against the opposing tissue wall 304, rather the balloon unfolds open from the internal aspect as it progresses. The rotation with balloon 306 unfolding from within is ideal for propagation of a vehicle within the lumen of the bowel, for example.

Figure 4C:
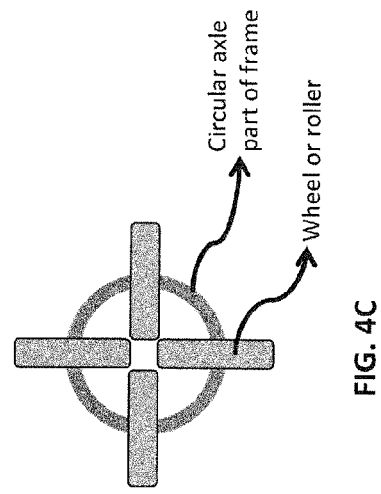
FIGS. 4A-D depict details of a structural frame with rollers that, in one embodiment, is disposed within a toroidal balloon to make a toroidal balloon driven vehicle.
Figure 4D:
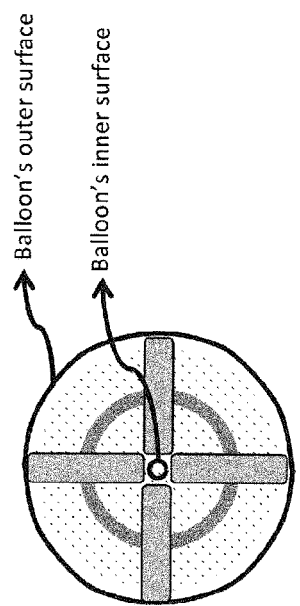
Figure 4A:
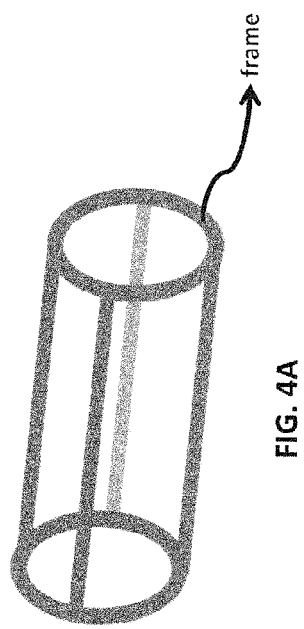
Figure 4B:
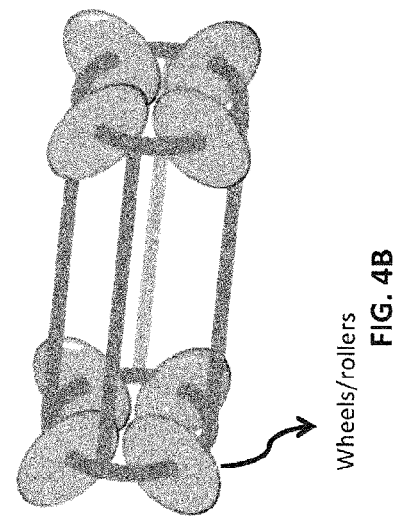

FIG. 4A depicts an example of a structural frame that is disposed within the toroidal balloon driven vehicle (TBDV) where the structural frame in a non-limiting example is cylindrical in shape. FIG. 4B depicts the structural frame of FIG. 4A with wheels or rollers mounted in them. FIG. 4C and FIG. 4D depict a cross sectional view of frame and wheels/rollers without the toroidal balloon and with the toroidal balloon, respectively.

Figure 5:
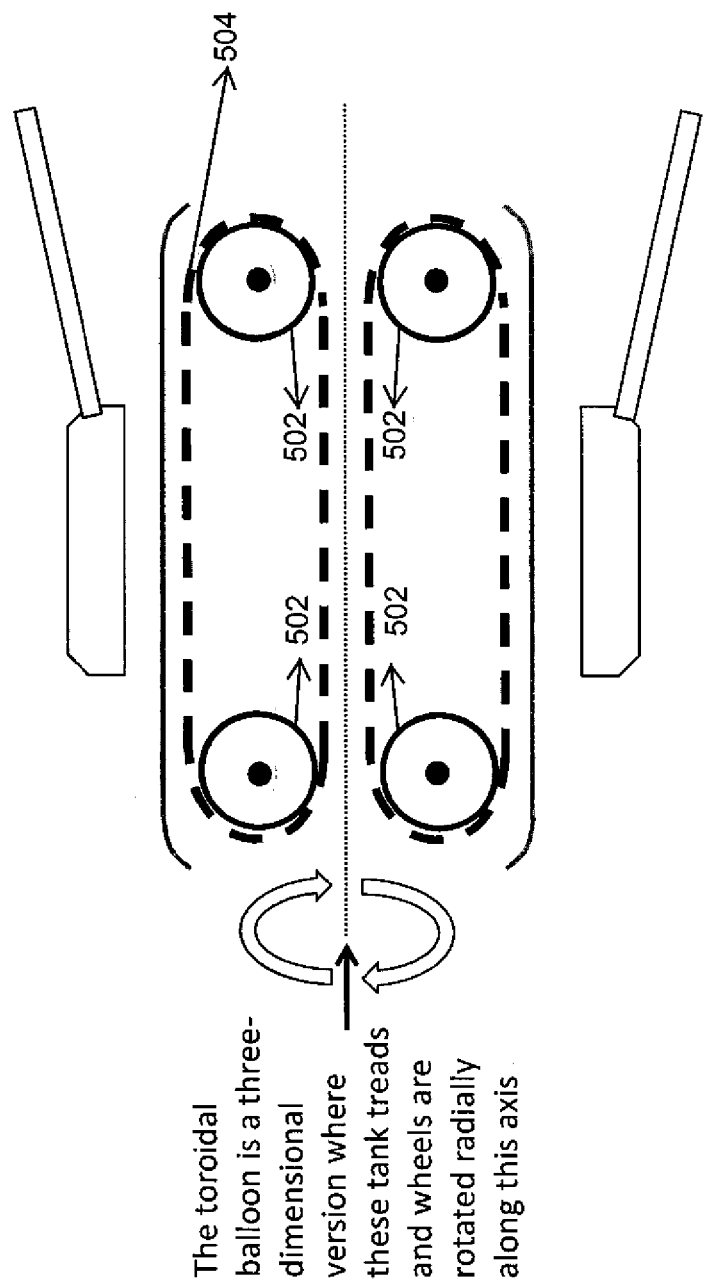
FIG. 5 depicts, for further demonstration, a two-dimensional example using two military tanks to describe the rotation of the toroidal balloon that propels the TBDV forward.

FIG. 5 depicts an example of the present invention's toroidal balloon that is draped over the wheels so that the balloon rotates along with rotation of the wheels 502. Note that a "wheel" 502 may exist as any circular roller that rotates on the frame and is arranged in a configuration with other rollers to guide and/or drive the rotating walls of the balloon. At least one motor rotates the driving wheel(s) 502 either directly using gears or via a system of belts or rotating axle(s). In the version of the TBDV without a utility component, the driving wheel(s) 502 is/are located within the balloon. It is not required that all wheels be attached to the motor (actively driven wheel). Some wheels (passively driven wheel) may serve as guides to the moving balloon and be rotated by the moving balloon itself. The frame keeps the rollers in direct opposition to the inner surface of the balloon and maintains the shape of the toroidal balloon. The frame also provides a location for attachment of structural components. A two-dimensional analogy of the toroidal balloon rotating over motor driven wheels is the rotating treads on the two military tanks, where a motor rotates the wheels and drives rotation of the treads. The ultimate placement and number of wheels on the frame as well as the configuration of the motor, drivetrain other components will depend upon the dimensions of the TBDV, the function of the TBDV and space requirements of the individual components. In this example with two military tanks, the tanks' motors rotate the wheels that rotate the tanks' treads in mirror-image synchrony, propelling the tanks forward. The tread on the present invention's TBDV can be created in three dimensions by radially rotating the tank treads in FIG. 5 around an axis that is the dotted line "ground" in FIG. 5. This three-dimensional tread becomes the toroidal balloon itself in a TBDV. The balloon is draped over the wheels so that the balloon rotates along with rotation of the wheels.

Figure 6A:
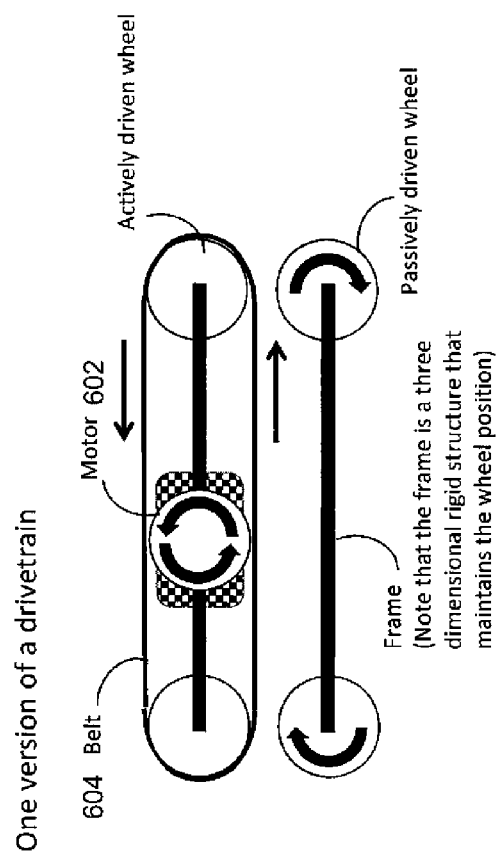
FIG. 6A and FIG. 6B depict a two-dimensional simplified diagram that demonstrates an example of a drivetrain with motor separately and within the toroidal balloon, respectively.
Figure 6A:
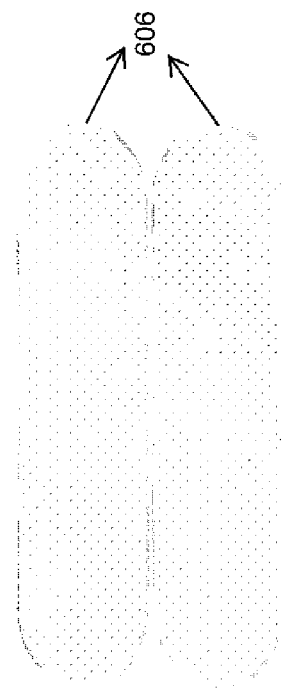
Figure 6B:
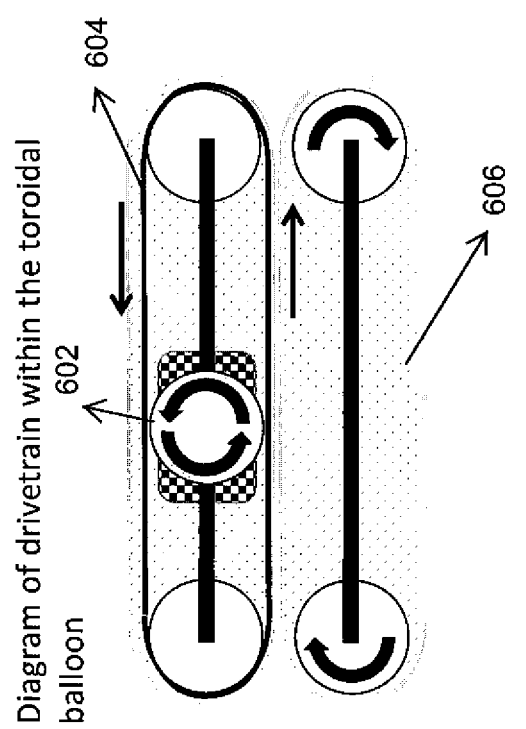

FIG. 6A and FIG. 6B depict a two-dimensional simplified diagram that demonstrates an example of a drivetrain with motor separately and within the toroidal balloon, respectively. In FIG. 6A, the first image shows the drivetrain without view of the balloon that consists of a motor 602 that moves the belt 604 which is translated into a motion of the toroidal balloon which causes the above-described inversion. The second image in FIG. 6A is of the toroidal balloon 606 by itself. In FIG. 6B, the drivetrain is located within the toroidal balloon, demonstrating the two images in FIG. 6A together.

In yet another embodiment, the present invention provides an apparatus comprising: a toroidal balloon comprising an internal balloon surface and an external balloon surface, the internal balloon surface of the toroidal balloon configured for contacting a utility component and the external balloon surface 706 of the toroidal balloon configured for contacting a biological wall; a utility component 702 disposed through the inner channel 704 of the toroidal balloon, a part of which extends outside the inner channel 704 of the toroidal balloon and is shaped to disallow the rotating TBDV to roll away from it; with or without a propelling mechanism comprising a controller, a motor and a plurality of rollers, where the controller instructs the motor to rotate the plurality of rollers to cause an inversion of the internal balloon surface and external balloon surface, the inversion configured to rotate the balloon without sliding of the external balloon surface against any contacted biological wall, but by allowing low friction sliding of the internal balloon surface of the toroidal balloon over the utility vehicle, and wherein one or more of the following are disposed on the utility component part 702 outside the toroidal balloon: a camera, a light source, a subset of the plurality of rollers with or without drivetrain, other therapeutic, diagnostic or utility components.

Figure 7A:
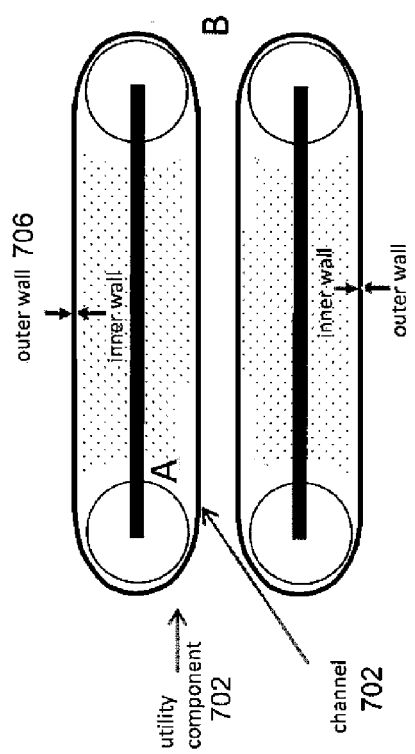
FIG. 7A depicts a two-dimensional example views in the coronal section of the present invention's toroidal balloon-driven vehicle with a utility component.
Figure 7B:
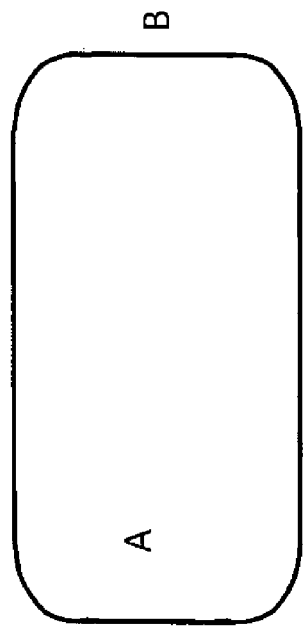
FIG. 7B depicts a three-dimensional example view from the outside of the present invention's toroidal balloon-driven vehicle with a utility component.
Figure 7C:
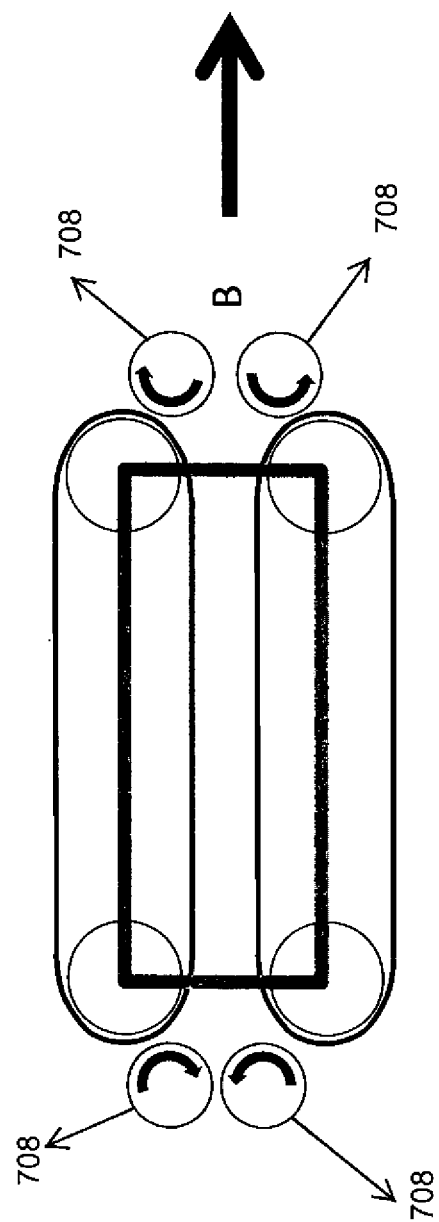
FIG. 7C depicts a two-dimensional simplified diagram that demonstrates the TBDV with a utility component that contains rollers to drive the rotation of the rollers within the TBDV.

FIGS. 7A-B show an example of the present invention's toroidal balloon-driven vehicle with the above-described utility component. FIG. 7A shows a coronal view of the device with the utility component and FIG. 7B shows an external view of the device with the utility component disposed within a channel formed by the outer walls, where the toroidal balloon in three-dimensions appears like a cylinder. FIG. 7C depicts another embodiment of the TBDV where a plurality of power-driven wheels 708 are located on the utility component.

In one embodiment, the present invention's toroidal balloon-driven vehicle or utility component may contain a mechanism for remote communication and remote operation.

Figure 8B:
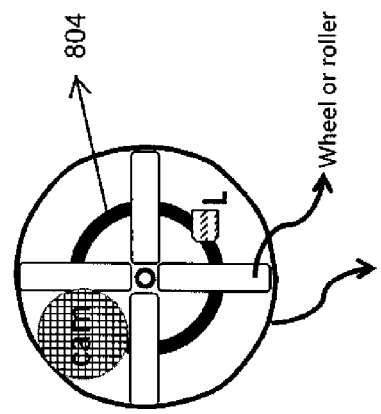
FIGS. 8A-B depict example views of the present invention's toroidal balloon-driven vehicle (TBDV) with cameras (cam) and light sources (L).
Figure 8D:
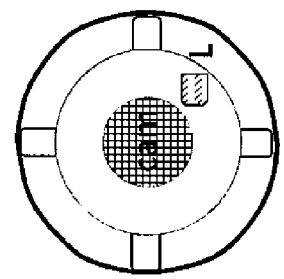
FIGS. 8C-D depict the present invention's TBDV with cameras (cam) and light sources (L) contained within the utility component.
Figure 8A:
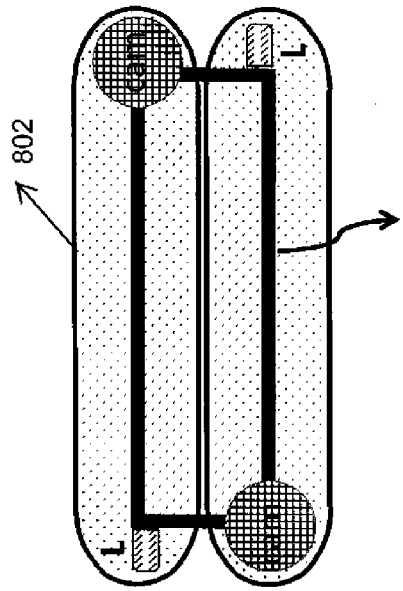

In one embodiment, the present invention's toroidal balloon-driven vehicle may contain at least one camera and at least one light source "L" where the camera(s) "cam" are located within the transparent balloon 802 and attached to the structural frame 804. FIG. 8A depicts a coronal view of such an example where there are two cameras "cam" (one on each end) and two light sources "L" (one at each end), where the cameras "cam" and the lights "L" may be mounted on the previously described frame, where the balloon in this instance may at least be partially clear to allow image/video capture and to allow light to pass from each of the light sources. FIG. 8B depicts a front view of the device shown in FIG. 8A.

Figure 8C:
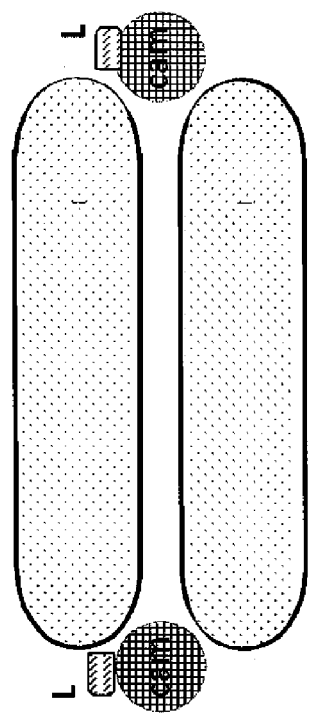

In one embodiment, the present invention's toroidal balloon-driven vehicle may contain at least one camera "cam" and light source "L" where the camera(s) "cam" are located on an associated device (e.g., on an associated device like the above-described utility component that is outside of the toroidal balloon). FIG. 8C depicts a coronal view of such an example where there are two cameras "cam" (one on each end) and two light sources "L" (one at each end) located on, for example, a utility component. FIG. 8D depicts a front view of the device shown in FIG. 8C.

Figure 9A:
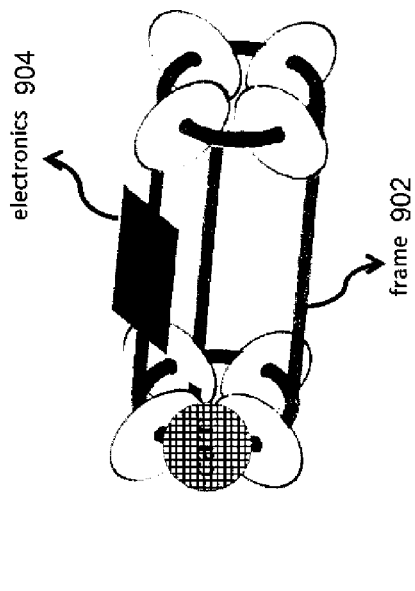
FIG. 9A depicts another example of the toroidal balloon-driven vehicle where the camera (cam) and other electronic or mechanical components may be attached to the frame.
Figure 9B:
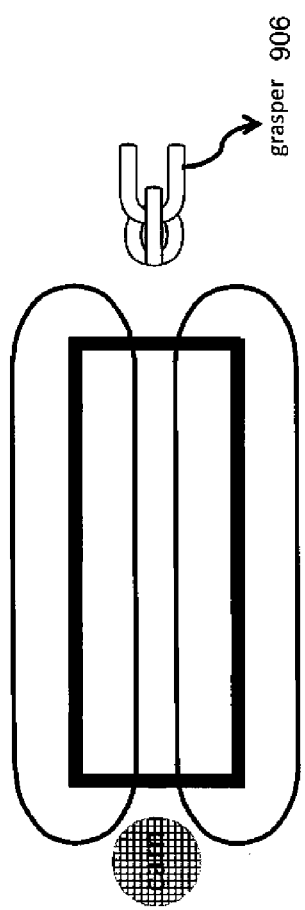
FIG. 9B depicts another example of the toroidal balloon-driven vehicle where it is constructed with a utility component, so that other components, like a grasper, may be attached to the utility component.

FIG. 9A depicts another example of the toroidal balloon-driven vehicle where the camera (labeled "cam" in the figure) and other electronic 904 or mechanical components may be attached to the frame 902. FIG. 9B depicts another example of the toroidal balloon-driven vehicle in coronal section where it is constructed with a utility component, so that other components, like a grasper, may be attached to the utility component.

In the examples above including at least one camera, the present invention's toroidal balloon-driven vehicle may contain electronic memory, for example, to store images or video captured by the camera.

In one embodiment, the present invention's toroidal balloon-driven vehicle may contain a source of energy such as, but not limited to, a battery or other power sources.

In one embodiment, the present invention's toroidal balloon-driven vehicle may contain a radio-opaque marker for location with x-rays.

In one embodiment, the present invention's toroidal balloon driven vehicle may contain a beacon for determination of physical location that uses global positioning, triangulation technology or other localization techniques such as in the example of a toroidal balloon-driven vehicle designed to remotely explore a burning house or examine the lumen of a gas pipeline.

In one embodiment, the present invention's toroidal balloon-driven vehicle may contain a chamber to hold or release compressed gas, liquid or solid, or be associated with a utility component containing such a chamber. An example would be a pressurized gas tank with remotely controlled valve attached to the structural frame within the toroidal balloon that could inflate the toroidal balloon to dilate an area of stenotic bowel or to tamponade a bleeding area of bowel mucosa. Another example is a remotely controlled chamber within the associated utility component that could release a drug in liquid or solid form.

In one embodiment, the present invention's toroidal balloon-driven vehicle may contain a mechanism to alter its geometry such as length, diameter and shape. For example, the frame may be constructed with a mechanical component that changes the frame's dimensions, where the length of the frame may be shortened with a small motor and gear apparatus, or the position of a wheel may be changed by a mechanism to move its axle relative to the frame.

The present invention's toroidal balloon-driven vehicle can be fashioned for both diagnostic and therapeutic purposes such as, but not limited to, examination, injection, cauterization, infusion, division, irrigation, marking or tattooing, tamponade, biopsy, sampling, delivery of a source of radiation, delivery of a medication or biologically active substance, alter local temperature, delivery of an ultrasonic probe, delivery of a magnetic resonance imaging probe, delivery of a radio frequency ablation probe, delivery of a cryotherapy probe, delivery of an endoscope, delivery of the tip of a flexible biopsy forceps, delivery of a medical instrument.

The present invention's toroidal balloon-driven vehicle may transport another device such as a utility component fashioned for both diagnostic and therapeutic purposes such as, but not limited to, examination, injection, cauterization, infusion, division, irrigation, marking or tattooing, tamponade, biopsy, sampling, delivery of a source of radiation, delivery of a medication or biologically active substance, alter local temperature, delivery of an ultrasonic probe, delivery of a magnetic resonance imaging probe, delivery of a radio frequency ablation probe, delivery of a cryotherapy probe, delivery of an endoscope, delivery of the tip of a flexible biopsy forceps, delivery of a medical instrument.

The present invention's toroidal balloon-driven vehicle may exist by itself or be connected to a device that manipulates surrounding or proximate tissue or objects. For example, a TBDV may have a simple configuration unassociated with a utility component for examination of the small bowel, similar to pill endoscopy, however with the ability to actively "drive" to a certain area and be able to change direction. To manipulate surrounding tissue, the TBDV may be associated with a remotely controlled utility component that can cut or biopsy abnormal tissue.

The present invention's toroidal balloon-driven vehicle can serve other purposes outside of the medical field where this form of rotating balloon propulsion is beneficial such as in industry, general commercial and residential application or the military. The unique quality of the TBDV is that virtually the entire external surface of the vehicle is the tread itself, minimizing exposed areas of the vehicle that may get stuck to or inhibited by its surroundings.

Figure 10:
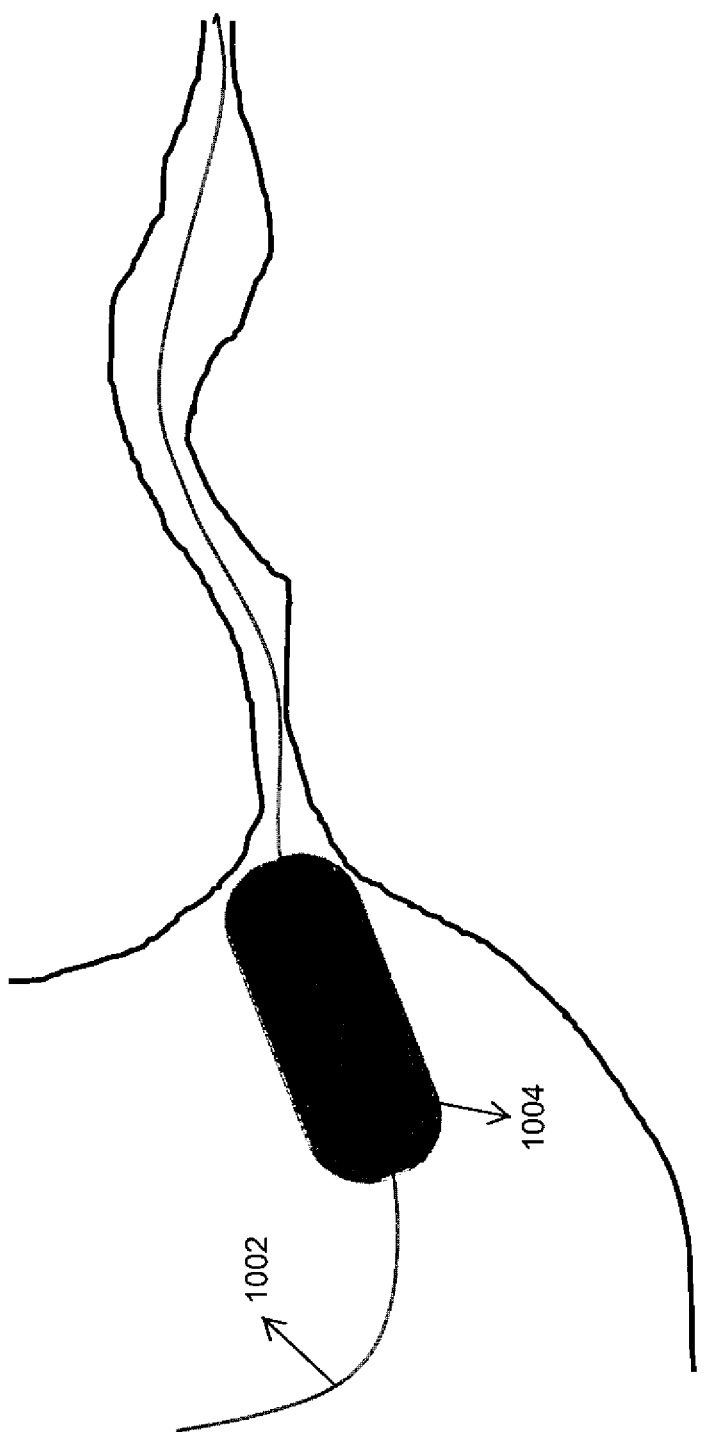
FIG. 10 depicts an example where the toroidal balloon-driven vehicle is guided by a lubriciously coated glide wire from the stomach into the small bowel for a remotely controlled camera enteroscopy.

The present invention's toroidal balloon-driven vehicle may be guided along its intended path using a guide or track such as, but not limited to, a lubriciously-coated wire. FIG. 10 depicts such an example where the toroidal balloon-driven vehicle 1004 is guided by a lubriciously coated glide wire 1002 from the stomach into the small bowel for a remotely controlled camera enteroscopy.

The present invention's toroidal balloon-driven vehicle may be guided by a magnet and thus contain a magnet of ferromagnetic material in its construction.

The present invention's toroidal balloon-driven vehicle may be placed into position at the end of a placement device such as an endoscope, catheter, wire or probe.

The present invention's toroidal balloon-driven vehicle may be driven-off the end of the placement device.

The present invention's toroidal balloon-driven vehicle may be either disposable or reusable.

Figure 11:
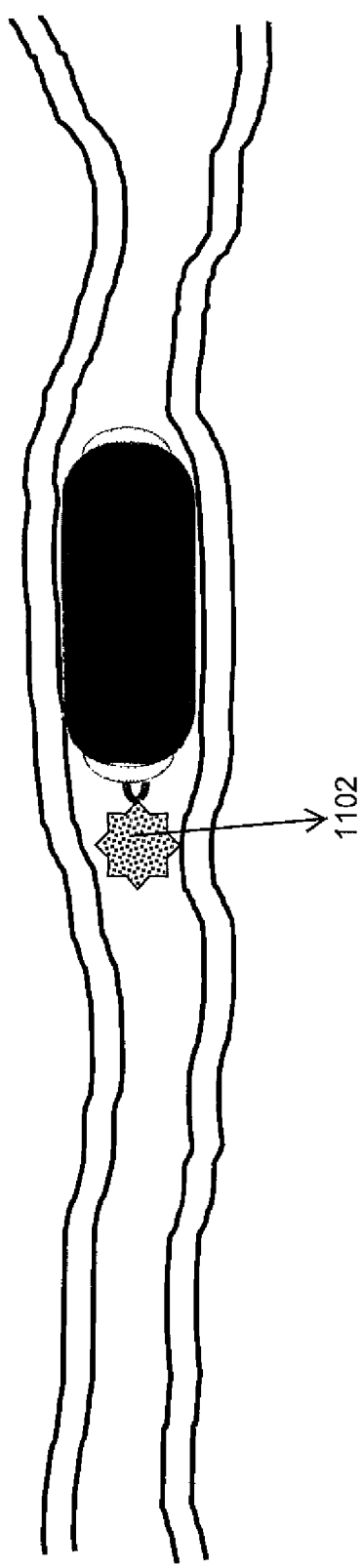
FIG. 11 depicts an example where the toroidal balloon-driven vehicle with a utility component is used to deliver a biologically active substance to the small bowel.

The present invention's toroidal balloon-driven vehicle may be used to deliver an active substance. FIG. 11 depicts such an example where the toroidal balloon-driven vehicle with a utility component is used to deliver a biologically active substance 1102 to the small bowel.

Figure 12A:
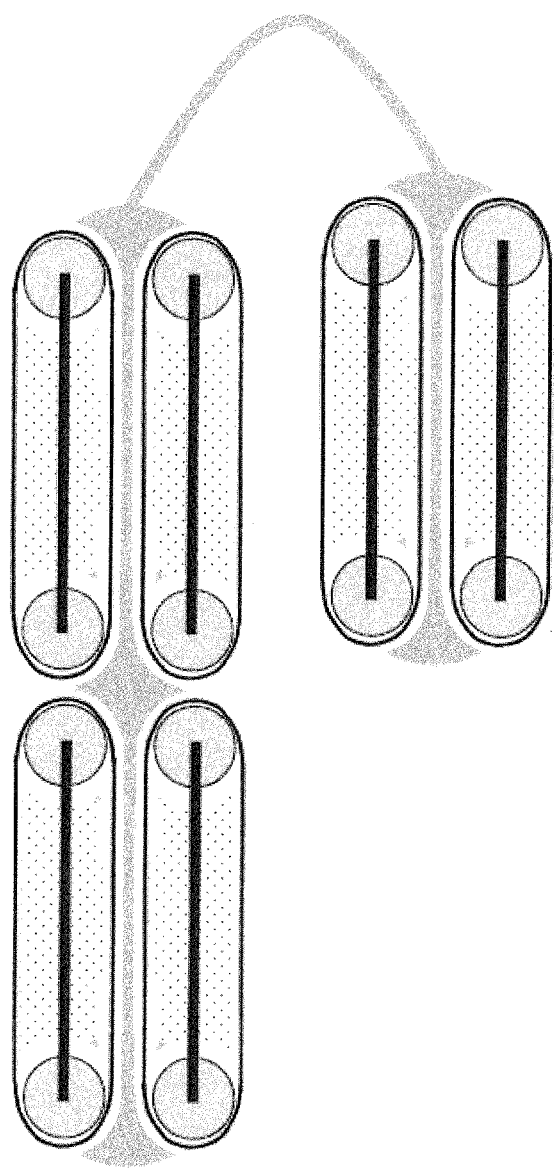
FIGS. 12A-B depict how a plurality of TBDVs are linked in serial and parallel, respectively.
Figure 12B:
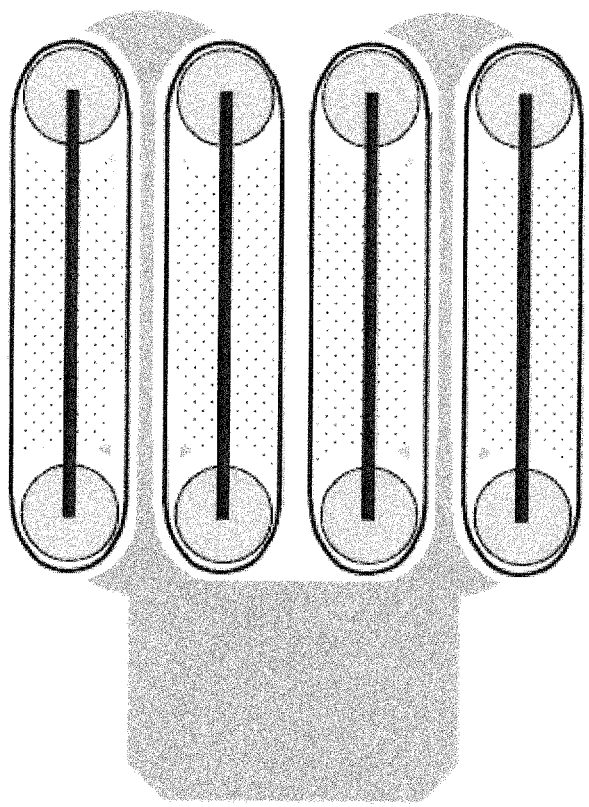

The present invention's toroidal balloon-driven vehicle may consist of multiple balloons either in series or in parallel. For example, the TBDV may have a utility component connected to, or capable of connecting to, another TBDV's utility component in a serial arrangement, as shown in FIG. 12A, similar to boxcars on a train. An example of TBDVs in parallel would involve utility components with a rigid connection, as depicted in FIG. 12B, to maintain the orientation of the TBDVs.

Further, while not described explicitly in the various embodiments noted above, the present invention's toroidal device may contain memory or computer storage for storing instructions that are to be executed by the controller.

CONCLUSION

A system and method has been shown in the above embodiments for the effective implementation of a toroidal device-driven vehicle. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:

1. A medical apparatus comprising:
  a self-contained, transparent toroidal device comprising an inner device surface and an outer device surface, the inner and outer device surfaces comprising inner walls and outer walls configured to form a toroid, where a portion of the outer walls associated with the inner device surface are adjacent to each other and are configured to form a channel, and where another portion of the outer walls associated with the outer device surface are configured to contact an external wall; and
  an internal propelling mechanism located entirely within the inner walls of the transparent toroidal device and configured for inverting the inner device surface and outer device surface, with the inversion safely propelling the apparatus without sliding of the outer device surface against any contacted external wall and allowing low friction movement of the apparatus with rotation of the toroidal device, the internal propelling mechanism comprising: a controller, a structural frame with a plurality of rollers disposed thereon, and at least one motor,
  wherein the controller instructs the motor to rotate the plurality of rollers to cause the inversion of the inner device surface and the outer device surface, with the inversion propelling the apparatus forward or backward without sliding the outer device surface against any contacted external wall.

2. The medical apparatus of claim 1, wherein the toroidal device is a toroidal balloon.

3. The medical apparatus of claim 1, wherein the external wall is part of a tubular wall.

4. The medical apparatus of claim 1, wherein the external wall is a biological wall.

5. The medical apparatus of claim 1, wherein the structural frame comprises a drivetrain frame, with at least the controller and the plurality of rollers disposed on the drivetrain frame.

6. The apparatus of claim 1, wherein the apparatus further comprises at least one light source and at least one camera disposed within the inner walls.

7. The medical apparatus of claim 1, wherein the apparatus further comprises a utility component, where a portion of the utility component is located inside the channel and a remainder portion of the utility component located outside the channel.

8. The apparatus of claim 7, wherein the apparatus comprises at least one additional roller located on the remainder portion of the utility component located outside the channel.

9. The apparatus as per claim 7, wherein the apparatus is serially linked with another similar apparatus via a common utility component.

10. The apparatus as per claim 7, wherein the apparatus is linked in parallel with another similar apparatus via a link that couples utility component of the apparatus and the another similar apparatus.

11. The apparatus of claim 7, wherein the apparatus comprises at least one light source and at least one camera located on the remainder portion of the utility component located outside the channel.

12. The apparatus as per claim 1, wherein the apparatus is further attached to a medical instrument.

13. The apparatus as per claim 1, wherein the apparatus further comprises a transceiver for remote communication and control of the apparatus, the remote control based on instructions received via the transceiver.

14. The apparatus as per claim 1, wherein the apparatus comprises a radio-opaque marker for location of the apparatus.

15. The apparatus as per claim 1, wherein the apparatus further comprises a chamber to hold or release any one of, or a combination of, the following: compressed gas, liquid or solid.

16. The apparatus as per claim 1, wherein the apparatus further comprises a location reporting system to report location of the apparatus.

17. The apparatus as per claim 1, wherein at least a portion of the apparatus is constructed from ferromagnetic material where the apparatus is configured to additionally be guided by a magnet.

18. The medical apparatus as per claim 1, wherein the apparatus is disposable.

19. The apparatus as per claim 1, wherein the apparatus is initially positioned via any of the following: a probe, a scope, or a catheter.

20. The medical apparatus as per claim 1, wherein at least a portion of the apparatus is made from any of the following: nylon or a material allowing low friction rotation of the toroidal device over the internal propelling mechanism.

21. A medical apparatus comprising:
a self-contained, transparent, toroidal balloon comprising an inner balloon surface and an outer balloon surface, the inner and outer balloon surfaces comprising inner walls and outer walls configured to form a toroid, where a portion of the outer walls associated with the inner balloon surface are adjacent to each other and are configured to form a channel, and where another portion of the outer walls associated with the outer balloon surface are configured to contact an external wall; and
an internal propelling mechanism located entirely within the inner walls of the toroidal balloon and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising: a controller, a structural frame with a plurality of rollers disposed thereon, and at least one motor,
wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

22. The medical apparatus of claim 21, wherein the external wall is part of a tubular wall.

23. The medical apparatus of claim 21, wherein the external wall is a biological wall.

24. The medical apparatus of claim 21, wherein the structural frame comprises a drivetrain frame, with at least the controller and the plurality of rollers disposed on the drivetrain frame.

25. The apparatus of claim 21, wherein the apparatus further comprises at least one light source and at least one camera disposed within the inner walls.

26. The medical apparatus of claim 21, wherein the apparatus further comprises a utility component, where a portion of the utility component is located inside the channel and a remainder portion of the utility component located outside the channel.

27. The apparatus of claim 26, wherein the apparatus comprises at least one additional roller located on the remainder portion of the utility component located outside the channel.

28. The apparatus as per claim 26, wherein the apparatus is serially linked with another similar apparatus via a common utility component.

29. The apparatus as per claim 26, wherein the apparatus is linked in parallel with another similar apparatus via a link that couples utility component of the apparatus and the another similar apparatus.

30. The apparatus of claim 26, wherein the apparatus comprises at least one light source and at least one camera located on the remainder portion of the utility component located outside the channel.

31. The apparatus of claim 21, wherein the apparatus is further attached to a medical instrument.

32. The apparatus of claim 21, wherein the apparatus further comprises a transceiver for remote communication and control of the apparatus, the remote control based on instructions received via the transceiver.

33. The apparatus of claim 21, wherein the apparatus comprises a radio-opaque marker for location of the apparatus.

34. The apparatus of claim 21, wherein the apparatus further comprises a chamber to hold or release any one of, or a combination of, the following: compressed gas, liquid or solid.

35. The apparatus of claim 21, wherein the apparatus further comprises a location reporting system to report location of the apparatus.

36. The apparatus as per claim 21, wherein at least a portion of the apparatus is constructed from ferromagnetic material where the apparatus is configured to additionally be guided by a magnet.

37. The medical apparatus as per claim 21, wherein the apparatus is disposable.

38. The apparatus as per claim 21, wherein the apparatus is initially positioned via any of the following: a probe, a scope, or a catheter.

39. A medical apparatus comprising:
a self-contained, transparent, toroidal balloon comprising an inner balloon surface and an outer balloon surface, the inner and outer balloon surfaces comprising inner walls and outer walls configured to form a toroid, where a portion of the outer walls associated with the inner balloon surface are adjacent to each other and are configured to form a channel, and where another portion of the outer walls associated with the outer balloon surface are configured to contact an external wall;

an internal propelling mechanism located entirely within the inner walls of the toroidal balloon and configured for inverting the inner balloon surface and outer balloon surface, with the inversion safely propelling the apparatus without sliding of the outer balloon surface against any contacted external wall and allowing low friction movement of the apparatus with rotation of the toroidal balloon, the internal propelling mechanism comprising a structural frame with a plurality of rollers disposed thereon;

a utility component, where a portion of the utility component is located inside the channel and a remainder portion of the utility component located outside the channel, wherein a controller and a motor are provided in said internal propelling mechanism and/or in said utility component, and wherein the controller instructs the motor to rotate the plurality of rollers to cause the inversion of the inner balloon surface and the outer balloon surface, with the inversion propelling the apparatus forward or backward without sliding the outer balloon surface against any contacted external wall.

40. The apparatus as per claim 39, wherein one or more of the following components are located on the utility component: one or more additional rollers, one or more light sources, one or more cameras, and one or more graspers.

41. The apparatus as per claim 39, wherein the apparatus is serially linked with another similar apparatus via a common utility component.

42. The apparatus as per claim 39, wherein the apparatus is linked in parallel with another similar apparatus via a link that couples utility component of the apparatus and the another similar apparatus.

43. The medical apparatus as per claim 39, wherein the structural frame comprises a drivetrain frame, with at least the controller and the plurality of rollers disposed on the drivetrain frame.

44. The apparatus as per claim 39, wherein the apparatus is further attached to a medical instrument.

45. The apparatus as per claim 39, wherein the apparatus further comprises a transceiver for remote communication and control of the apparatus, the remote control based on instructions received via the transceiver.

46. The apparatus as per claim 39, wherein the apparatus comprises a radio-opaque marker for location of the apparatus.

47. The apparatus as per claim 39, wherein the apparatus further comprises a chamber to hold or release any one of, or a combination of, the following: compressed gas, liquid or solid.

* * * * *